United States Patent [19]
Jehle et al.

[11] Patent Number: 5,269,933
[45] Date of Patent: Dec. 14, 1993

[54] METHOD FOR SEPARATING A FLUID MIXTURE

[75] Inventors: Walter Jehle, Horgenzell; Guido Schäffner, Überlingen, both of Fed. Rep. of Germany

[73] Assignee: Dornier GmbH, Fed. Rep. of Germany

[21] Appl. No.: 951,010

[22] Filed: Sep. 25, 1992

[51] Int. Cl.⁵ .................... B01D 15/00; B01D 61/00
[52] U.S. Cl. ................... 210/640; 210/652; 210/805; 210/807; 210/651; 203/11; 203/12; 203/14
[58] Field of Search ............ 210/640, 651, 652, 805, 210/654, 807, 195.2; 203/10, 11, 12, 14, 18, 21

[56] References Cited

U.S. PATENT DOCUMENTS

| | | | |
|---|---|---|---|
| 3,574,772 | 4/1971 | Becker et al. | 203/18 |
| 4,000,065 | 12/1976 | Ladha et al. | 210/651 |
| 4,332,643 | 6/1982 | Reid et al. | 203/18 |
| 4,405,409 | 9/1983 | Tusel et al. | 203/21 |
| 4,622,104 | 11/1986 | Néel et al. | 203/18 |
| 4,888,189 | 12/1989 | Gnekow | 210/652 |
| 4,959,151 | 9/1990 | Nakatani et al. | 210/640 |
| 4,978,430 | 12/1990 | Nakagawa et al. | 203/18 |
| 4,997,462 | 3/1991 | Nakatani et al. | 210/640 |
| 5,059,327 | 10/1991 | Takegami | 210/640 |
| 5,108,549 | 4/1992 | Wenzlaff et al. | 203/14 |
| 5,182,022 | 1/1993 | Pasternak et al. | 210/640 |

FOREIGN PATENT DOCUMENTS 0104025 6/1985 Japan .................. 210/651

*Primary Examiner*—Robert A. Dawson
*Assistant Examiner*—Ana M. Fortuna
*Attorney, Agent, or Firm*—Evenson, McKeown, Edwards & Lenahan

[57] ABSTRACT

An improved method is provided for separation of a mixture of an organic fluid and water. The method is a combination of a distillation, an $H_2O$-selective pervaporation and a reverse osmosis and is particularly suitable for the separation of glycol and water.

11 Claims, 1 Drawing Sheet

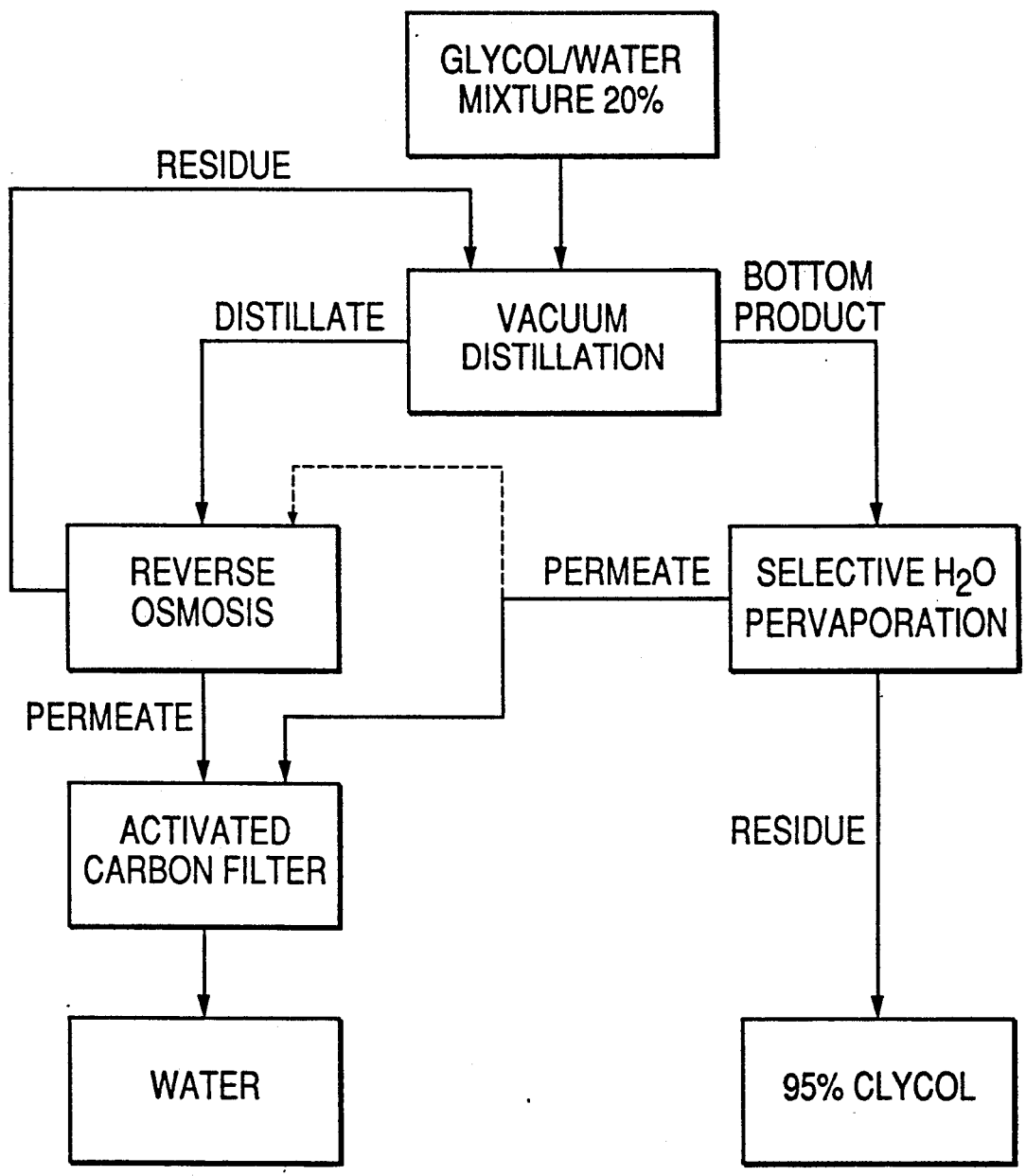

METHOD FOR SEPARATING A FLUID MIXTURE

BACKGROUND AND SUMMARY OF THE INVENTION

The present invention relates to a process for separating a mixture of an organic fluid and water, and, more particularly, to a process that involves distillation of the mixture, $H_2O$-selective pervaporation and application of reverse osmosis to the distillate.

In Germany alone, several tens of thousands of tons of spent glycol solutions having a concentration of approximately 20% are generated each year by automobile radiators. In the future, it will no longer be permitted that the spent contents of the radiators are directed to the sewage treatment plants but they must be treated as special refuse. A considerable demand therefore exists for a cost-effective possibility of a disposal and recycling of the substances.

A pure distillation method for the separation of the glycol has several disadvantages. For example, because of various components, there is the danger that nitrosamines may be formed at temperatures of above 80° C. This can only be avoided by a high-expenditure complete removal of nitrite and nitrate. For achieving a high purity of the distillate, a high recycle ratio is required which, however, can be achieved only with a high consumption of energy. Moreover, the bottom product formed during the distillation has to be removed separately.

From an economical point of view, regeneration exclusively according to the known pervaporation method is not suitable because the membrane surface required would be very large and expensive.

It is an object of the present invention, therefore, to provide an economical method for the separation of a mixture of water and an organic fluid, particularly glycol, in which case the separated water is obtained with such high purity that reuse or an unlimited introduction is possible.

This object has been achieved by a method in accordance with the present invention in which occurs distilling the mixture; performing an $H_2O$-selective pervaporation to bottom product obtained from the distillation step to obtain a residue and permeate; applying a reverse osmosis to at least the distillate to obtain a residue and permeate; and feeding the residue obtained from the reverse osmosis for performing thereon the distillation step, such that segregated organic fluid is present as residue from the $H_2O$-selective pervaporation, and segregated water is present as the permeate from the $H_2O$-selective pervaporation step as well as the permeate from the reverse osmosis step.

The method according to the present invention, which, as stated above, combines the processes of distillation, with one of pervaporation and reverse osmosis, is, of course, to be clearly understood that the process of the present invention is not limited to the separation of glycol from water. It can be used in general for the separation of fluid mixtures consisting of water and an organic fluid, such as carboxylic acids, including, for example, ethanoic acid, propionic acid; aromatic amines, including, for example, aniline; phenol; and glycerin.

It is a prerequisite for the utilization of the method according to the present invention that such organic fluids are used which can be separated from water by each of the three individual processes of distillation, selective $H_2O$-pervaporation and reverse osmosis. The parameters to be determined for the feasibility of a distillation process is the temperature of ebullition (boiling) of the two substances to be separated. In contrast, for the feasibility of a reverse osmosis process, the molar mass is of great importance.

The method according to the present invention can be used for such organic fluids whose temperatures of ebullition (or boiling) in the case of the respective pressure are higher than that of water, and whose molar mass is above 40 g/mol. The state-of-the-art of suitable membranes for carrying out an $H_2O$-selective pervaporation has nowadays reached such a high level of sophistication that a suitable membrane is available for any organic fluid.

The method of the present invention permits the organic fluid, which is preferably present in a concentration range of from about 5 to 70%, to be enriched to a concentration of at least 90%, preferably equal to or greater than ($\geq$) 95%. At the same time, the segregated water is present with a purity of at least 99.9% and is therefore reusable to an unlimited extent.

According to the present invention, a distillation of the mixture takes place first. Preferable parameters of the process are in this example a temperature of 70° C.-160° C. and a pressure of 100 mbar-1,000 mbar. The distillation may be carried out at a normal pressure as well as at a reduced pressure (i.e. vacuum distillation).

The next step is the concentration of the organic fluid by the application of a pervaporation with the use of water-selective membranes to the bottom product obtained from the distillation. In this case, the preferred parameters of the process are a temperature of 60° C.-95° C., and a permeate-side pressure of 20-150 mbar.

The treatment of the water obtained from the distillate takes place by reverse osmosis. The obtained residue is returned into the feed of the distillation. Preferred parameters of the process in the case of the reverse osmosis are a temperature of 15° C.-35° C. and a pressure of 20-70 bar.

The separated organic fluid is present in the permeate obtained from the pervaporation with a concentration of at least 90%, preferably $\geq$95%. The separated water is present as a permeate obtained from the reverse osmosis and as a permeate obtained from the pervaporation. Advantageously, the permeate from the pervaporation can be introduced into the feed of the reverse osmosis in order to increase the purity of the water contained therein. The separated water is further treated by an activated carbon filter.

The method according to the present invention is particularly advantageous from a technical point of view (i.e., the products are a high-quality concentrate as well as a reusable high-purity water) as well as from an economical point of view (low energy requirement, low investment). In particular, the necessary structure for carrying out the method can be adapted to the respectively existing economical/technical conditions and can be optimized. Should, in the future, for example, the pervaporation prove to be particularly cost-effective (e.g., better, less expensive membranes than previously), it will be possible to expand the pervaporation within the overall method and to reduce the expenditures for the distillation process. Likewise, it is possible, should the reverse osmosis develop into a much more effective and more economical process, to increase the expenditures for the reverse osmosis and to reduce the expenditures in the distillation and the pervaporation steps. That is, the demands on the distillate and on the permeate can be reduced.

BRIEF DESCRIPTION OF THE FIGURE

The present invention will be explained in detail by way of a sole figure which is a schematic representation of the method using the example of the recovery of glycol from used radiator contents.

DETAILED DESCRIPTION OF THE DRAWING

After solid substances and undesirable ions are removed from used radiator water in a known manner, a water/glycol fluid mixture, which normally is present with a glycol concentration of from 20-30%, is subjected to a vacuum distillation. As a result of the good separation factor (a=50) because of the large difference of the ebullition temperatures, the water obtained in the distillate has a purity of 99%. The bottom product is drawn with a concentration of at least 60% glycol. In the case of a vacuum of 100 mbar, advantageously, temperatures of from about 70°-80° C. will be reached.

In the next stage, the glycol is concentrated in a pervaporation system by water-selective membranes. It is obtained in the residue with a purity of at least 95%. According to the concentration of the water in the permeate (a purity of the water of at least 99.95% is achievable) and the type of use, the water may be subjected to an additional purification.

The treatment of the water from the distillate and possibly from the permeate of the pervaporation is carried out in a reverse osmosis. The residue obtained here contains a glycol concentration which is higher than the feed approximately by a factor of 10. The residue is returned to the feed of the distillation. If required, the obtained water is then guided through an activated carbon filter.

When, for example, a glycol-water mixture with a 20% proportion of glycol is to be separated, based on a mass flow rate of 50 kg/h, the following mass flow rates and concentrations are obtained mathematically:

| | |
|---|---|
| Feed for the distillation | 53.94 kg/h with 18.59% glycol |
| Bottom product = feed for pervaporation | 14.28 kg/h with 70.00% glycol |
| Residue from pervaporation | 10.50 kg/h with 95.00% glycol |
| Permeate from pervaporation | 3.77 kg/h with 0.50% glycol |
| Distillate | 39.66 kg/h with 0.50% glycol |
| Feed for reverse osmosis = distillate + permeate from pervaporation | 43.44 kg/h with 0.50% glycol |
| Residue from reverse osmosis | 3.95 kg/h with 5.00% glycol |
| Permeate from reverse osmosis | 39.49 kg/h with 0.05% glycol |

In the above calculated values, values were in each case used for the separation factor of the distillation and for the retaining rate in the case of the reverse osmosis and the pervaporation which can be achieved with commercially available equipment.

In lab tests, the following results were achieved when a one-stage reverse osmosis was carried out:

(a) membrane used: Membrane 810 of Torray Company

| Feed Concentration [%] | Flow [kg/(m2*h)] | Permeate Concentration [%] | Degree of Retention |
|---|---|---|---|
| 0.1 | 59.5 | 0.013 | 87.0 |
| 0.5 | 51.9 | 0.052 | 89.8 |
| 1.0 | 45.6 | 0.155 | 88.6 |
| 5.0 | 20.8 | 0.880 | 82.4 |

(b) membrane used: Desal 3B Membrane of Desalination Co.

| Feed Concentration [%] | Flow [kg/(m2*h)] | Permeate Concentration [%] | Degree of Retention |
|---|---|---|---|
| 0.1 | 33.3 | 0.016 | 85.0 |
| 0.5 | 35.1 | 0.053 | 89.5 |
| 1.0 | 21.1 | 0.126 | 87.4 |
| 5.0 | 12.4 | 1.450 | 71.0 |

The experiments concerning results (a) and (b) were each carried out at a pressure of 40 bar and a temperature of 20° C. by a glycol/water mixture.

In lab tests, the following results were achieved when a water-selective pervaporation was carried out:

| | |
|---|---|
| Feed concentration: | 90.0% |
| Flow: | 1.2 kg/(m2*h) |
| Permeate concentration: | 0.6% |
| Separation factor: | 1,546 |

The tests were carried out by a glycol/water mixture at a temperature of 80° C. and a permeate pressure of 20 mbar. A composite membrane from the University of Koln was used as the membrane.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. A method for separating a mixture comprising water and an organic fluid having a boiling point higher than water, comprising the steps of distilling the mixture to obtain a distillate product and a bottom product;

performing an $H_2O$-selective pervaporation to the bottom product obtained from the distillation step to obtain a first residue and permeate;

applying a reverse osmosis to at least the distillate product to obtain a second residue and permeate; and feeding the second residue obtained from the reverse osmosis step for performing thereon the distillation step, such that segregated organic fluid is present as residue from the $H_2O$-selective pervaporation, and segregated water of high purity is present as the permeate from the $H_2O$-selective pervaporation step as well as the permeate from the reverse osmosis step.

2. The method according to claim 1, further comprising the step of feeding the permeate from the $H_2O$-selective pervaporation for performing thereon the reverse osmosis step.

3. The method according to claim 1, wherein the distillation step is carried out as a vacuum distillation.

4. The method according to claim 3, further comprising the step of feeding the permeate from the H$_2$O-selective pervaporation for performing thereon the reverse osmosis step.

5. The method according to claim 1, further comprising the step of treating the segregated water with an active carbon filter.

6. The method according to claim 5, further comprising the step of feeding the permeate from the H$_2$O-selective pervaporation for performing thereon the reverse osmosis step.

7. The method according to claim 6, wherein the distillation step is carried out as a vacuum distillation.

8. The method according to claim 1, wherein the organic fluid is glycol contained in the mixture in a concentration of from 20 to 30%.

9. The method according to claim 8, further comprising the step of feeding the permeate from the H$_2$O-selective pervaporation for performing thereon the reverse osmosis step.

10. The method according to claim 9, wherein the distillation step is carried out as a vacuum distillation.

11. The method according to claim 10, further comprising the step of treating the segregated water with an active carbon filter.

* * * * *